United States Patent
Perez-Soler et al.

(10) Patent No.: US 6,696,079 B2
(45) Date of Patent: *Feb. 24, 2004

(54) DELIVERY AND ACTIVATION THROUGH LIPOSOME INCORPORATION OF DIAMINOCYCLOHEXANE PLATINUM(II) COMPLEXES

(75) Inventors: Roman Perez-Soler, Houston, TX (US); Abdul R. Khokhar, Houston, TX (US)

(73) Assignee: Board of Regents, The University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/168,799

(22) Filed: Oct. 8, 1998

(65) Prior Publication Data

US 2001/0036470 A1 Nov. 1, 2001

Related U.S. Application Data

(62) Division of application No. 08/764,095, filed on Dec. 6, 1996, now Pat. No. 5,843,475.

(51) Int. Cl.⁷ .................... A61K 9/127; A61K 33/24
(52) U.S. Cl. ................ 424/450; 424/649; 514/492
(58) Field of Search ................ 424/400, 649; 514/492; 264/4.1, 4.3

(56) References Cited

U.S. PATENT DOCUMENTS 3,904,663 A   9/1975   Tobe et al. .............. 260/429 R (List continued on next page.)

FOREIGN PATENT DOCUMENTS

EP   0113508   7/1984
EP   0130482   1/1985

(List continued on next page.)

OTHER PUBLICATIONS

Sun Oncology. 40 372–376, 1983.*

(List continued on next page.)

Primary Examiner—Gollamudi S. Kishore
(74) Attorney, Agent, or Firm—Pennie & Edmonds LLP

(57) ABSTRACT

Antitumor compositions are disclosed, as well as methods of preparing the compositions and methods of using them to inhibit tumor growth in mammals. The invention can take advantage of intraliposomal conversion of a platinum complex having the formula

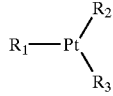

(I)

where $R_1$ is diaminocycloalkyl, and $R_2$ and $R_3$ each have the formula

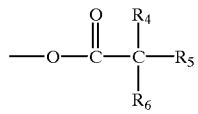

where $R_4$, $R_5$, and $R_6$ are each independently hydrocarbon moieties having from 1 to about 10 carbon atoms, into a complex having the formula

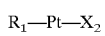

(II)

where X is halogen.

44 Claims, 9 Drawing Sheets

DACH Platinum(II) Complex

Phospholipids

R Group

1) NDDP: $C{-}R_2$ with $R_1, R_3$
   ($R_1+R_2+R_3=C_8H_{19}$)

2) B10: $C{-}(CH_2)_5CH_3$ with $CH_3, CH_3$

3) L10: $(CH_2)_8CH_3$

X Group

1) PC: $OCH_2CH_2{+}N(CH_3)_3$
2) PG: $OCH_2CHCH_2$ / $OHOH$
3) PA: OH
4) PE: $OCH_2CH_2{+}NH_3$
5) PS: $OCH(COO^-)(^+NH_3)$

U.S. PATENT DOCUMENTS

| | | | |
|---|---|---|---|
| 4,169,846 A | * 10/1979 | Kidani | |
| 4,200,583 A | 4/1980 | Kidani et al. | |
| 4,203,912 A | 5/1980 | Hydes et al. | 260/429 R |
| 4,230,631 A | 10/1980 | Hydes et al. | 260/429 R |
| 4,255,347 A | 3/1981 | Kidani et al. | 260/429 R |
| 4,256,652 A | 3/1981 | Kidani et al. | 260/429 R |
| 4,431,666 A | 2/1984 | Bulten et al. | 424/287 |
| 4,466,924 A | 8/1984 | Verbeek et al. | 260/429 R |
| 4,661,516 A | 4/1987 | Brown et al. | 514/492 |
| 4,758,588 A | 7/1988 | Brown et al. | 514/492 |
| 4,760,155 A | 7/1988 | Heffernan et al. | 556/136 |
| 4,760,157 A | 7/1988 | Child et al. | 556/137 |
| 4,845,124 A | 7/1989 | Kidani et al. | 514/492 |
| 4,861,905 A | 8/1989 | Nowatari et al. | 556/40 |
| 4,946,954 A | 8/1990 | Talebian et al. | |
| 4,956,459 A | 9/1990 | Talebian et al. | 536/121 |
| 5,011,959 A | 4/1991 | Khokhar et al. | 556/137 |
| 5,041,578 A | 8/1991 | Khokhar | 556/137 |
| 5,041,581 A | 8/1991 | Khokhar et al. | 556/137 |
| 5,117,022 A | * 5/1992 | Khokhar | |
| 5,178,876 A | * 1/1993 | Khokhar | |
| 5,186,940 A | 2/1993 | Khokhar et al. | 424/450 |
| 5,384,127 A | * 1/1995 | Perez-Soler | |
| 5,422,364 A | 6/1995 | Nicolau | 514/449 |

FOREIGN PATENT DOCUMENTS

| | | |
|---|---|---|
| EP | 0136012 | 4/1985 |
| EP | 0147926 | 7/1985 |
| EP | 0193936 | 9/1986 |
| EP | 0237450 | 9/1987 |
| EP | 0 193 936 B1 | 5/1989 |
| EP | 0356332 A2 | 2/1990 |
| WO | 87/02364 | 4/1987 |
| WO | 88/03925 | 6/1988 |
| WO | 90/02131 | 3/1990 |

OTHER PUBLICATIONS

Yatriw M Proc. Am. Assoc. Can Res 21 281 (Abstract, 1980).*

Han et al., 1996, "Intraliposomal conversion of lipophilic cis–bis–carboxylato–trans–R,R–1,2–diaminocyclohexane–platinum (II) complexes into cis–bis–dichloro–trans–R,R–1,2–diaminocyclohexane–platinum (II)", Cancer Chemother. Pharmacol. 39:17–24.

Han et al., Cellular pharmacology of liposomal cis–bis–neo-decanoato–trans–R,R–1,2–diaminocyclohexaneplatinum(II) in A2780/S and A2780/PDD cells. Cancer Res. 53:4913–19, 1993.

Han et al., Intraliposomal conversion of lipophilic 1,2–DACH–bisalkyl–platinum(II) complexes into DACH–Pt–Cl$_2$ (II). Proceed AACR 37:2740 p. 401, 1996.

Han et al., Liposomal–platinum (II) compounds (L–Pt): optimization of formulation parameters. Proceed AACR 35:2482 p. 416., 1994.

Hollis et al., cis–diamineplatinum (II) complexes containing phosphono carboxylate ligands as antitumor agents. J Med Chem. 33:105–11, 1990.

Ismail et al., $^{195}$Pt– and $^{15}$N–NMR studies of antitumor complexes. ACS Symposium Series, 209:171–190, 1983.

Khokhar et al., Chemical and biological studies on a series of lipid–soluble (trans–(R,R)– and –S,S)–1,2–Diaminocyclohexane) Platinum(II) Complexs Incorporated in Liposomes. J. Med. Chem. 34:325–329, 1991.

Khokhar et al., Toxicity and antitumor activity of cis–bis–carboxylato(trans–R,R–1,2–diaminocyclohexane) platinum(II) complexes entrapped in liposomes. Cancer Chemother Pharmacol. 23:219–24, 1989.

Khokhar et al., Toxocity and efficacy studies on a series of lipid–soluble dineodecnoato(trans–R,R– and trans–S,S–1, 2–diaminocyclohexane) platinum (II) complexes entrapped in liposomes. Anticancer Drugs. 3:95–100, 1992.

Li et al., Improved antitumor activity of cis–Bis–neode-canoato–trans–R,R–1,2–diaminocyclohexaneplatinum (II) entrapped in long–circulating liposomes. Oncology Res. 7:611–17, 1995.

Perez–Soler et al., Clinical development of Liposomal Platinum. J Lip Res. 1:437–449, 1990.

Perez–Soler et al., Increased cytotoxicity and reversal of resistance to cis–diamminedichloro–platinum(II) with entrapment of cis–Bis–neodecnoato–trans–R,R–1,2–diaminocyclohexaneplatinum (II) in multilamellar lipid vesicles. Cancer Res. 48:4509–12, 1988.

Perez–Soler et al., Lipophilic cisplatin analogues entrapped in liposomes: role of intraliposomal drug activation in biological activity. Cancer Res. 52:6341–47, 1992.

Perez–Soler et al., Lipophilic platinum complexes entrapped in liposomes: improved stability and preserved antitumor activity with complexes containing linear alkyl carboxylato leaving groups. cancer Chemother Pharmacol. 33:378–84, 1994.

Perez–Soler et al., Lipophilic cisplatin analogues entrapped in liposomes: role of chemical structure and liposome composition. Proceed AACR 32:2425 p. 408, 1991.

Perez–Soler et al., Lipophilic platinum compounds entrapped in liposomes: enhanced intraliposomal stability and preserved antitumor activity by using analogs with linear aliphatic leaving groups. Proceed AACR. 34:2182 p. 366, 1993.

Perez–Soler et al., Liposome–entrapped cis–bis–neode-canoato–trans–R,R–1,2–diaminocyclohexane platinum (II) (L–NDDP): effect of lipid composition on biological activity. Proceed AACR. 31:2542 p. 428, 1990.

Qu et al., Effect of diamine linker on the chemistry of Bis(Platinum) complexes. A comparison of the Aqueous solution behavior of 1,4–butanediamine and 2.5–dimethyl–2,5–Hexanediamine Complexes. J. Inorganic Biochem. 40:255–264., 1990.

Qu et al., Interaction of bis(platinum) complexes with the mononucleotide 5'–guanosine monophosphate. Effect of diamine linker and the nature of the bis(platinum) complex of product formation. J. Am. Chem. Soc. 113:4851–4857, 1991.

Slavin et al., Phosphonato complexes of platinum(II): kinetics of formation and phosphorus–31 NMR characterization studies. J Inorg Biochem. 40: 339–47, 1990.

Mori et al., In vivo antitumor activity of cis–bis–neode-canoato–trans–R,R–1,2–diaminocyclohexane platinum(II) formulated in long–circulating liposomes. Cancer Chemother Pharmacol. 37:435–44, 1996.

Schwartz, P. et al, "Preparation and Antitumor Evaluation of Water–Soluble Derivatives of Dichloro(1,2–diaminocyclohexane)platinum(II)", Cancer Treatment Reports, 61(8):1519–1525 (Nov., 1977).

Connors, T.A. et al, "New Platinum Complexes with Anti–Tumor Activity"Chem.–Biol. Interactions, 5:415–424 (1972).

Yatvin, M.B. et al, "Selective Delivery by Hyperthermia of Liposome Encapsulated Cis Dichlorodiamine Platinum (II) and Tumor Growth Delay", Abstract from Proc. Am. Assoc. Cancer Res., 21:281 (1980).

Deliconstantinos, G. et al, "Incorporation of Cis–Dichloro-biscyclopentylamineplatinum (II) into Liposomes Enhances its Uptake by Adj/PC6A Tumours Implanted Subcutaneously into Mice", Abstract from Biochem. Soc. Trans., 5(5):1326–1328 (1977).

Kaledin, V. et al, "Intralymphatic Administration of Liposome–Encapsulated Drugs to Mice: Possibility for Suppression of the Growth of Tumor Metastases in the Lymph Nodes", Jncl. 66(5):881–886 (May 1981).

Freise, J. et al, "Pharmacokinetics of Liposome Encapsulated Cisplatin in Rats", Archies Internationales de Pharmacodynamie et de Therapie, 258(2):180–192 (Aug. 1982).

Sur, B. et al, "Effect of liposomal encapsulation of cis–platinum diaminodichloride in the treatment of Ehrlich ascites carcinoma", Oncology, 40(5):372–376 (1983).

Yatvin, M.B. et al, "Selective Delivery of liposome–associated cis–dichlorodiamineplatinum (II) by heat and its influence on tumor drug uptake and growth", Cancer Research, 41(5):1602–1607 (May 1981).

Craciunescu, D.G. et al, "On the preparation, antitumour and cytotoxic evaluation of some new analogues of the cis–dichloro (1,2–diamino–cyclohexane) platinum (II) complex", Eur. J. Med. Chem.–Chem. Ther., 19:353–357 (1984).

Khokhar, A.R. et al, "The Synthesis and Antitumor Properties of a Series of Water Soluble carboxylato–(1,2–diaminocyclohexane) Platinum(II) Complexes", Inorganica chimica Acta, 108(1):63–66 (Sep. 1985).

Vollano, J.F. et al, "Comparative Antitumor Studies on Platinum(II) and Platinum(IV) Cmplexes Containing 1,2–Diaminocyclohexane", J. Med. Chem., 30:716–719 (1987).

Perez–Soler, R. et al, "Phase I Clinical and Pharmacological Study of Liposome–entrapped cis–Bis–neodecanoato–trans–R,R–1,2–diaminocyclohexane Platinum(II)", Cancer Research, 50(14):4254–4259 (Jul. 1990).

Ridgway, H.J. et al, "Analogs of Sulfato 1,2–Diaminocyclohexane Platinum(II) I Modifications in Leaving Ligand", Wadley Medical Bulletin, 7(1):220,229 (1977).

* cited by examiner

DACH Platinum(II) Complex

Phospholipids

R Group

1) <u>NDDP</u>:

$(R_1+R_2+R_3=C_8H_{19})$

2) <u>B10</u>:

3) <u>L10</u>: $(CH_2)_8CH_3$

X Group

1) <u>PC</u>: $OCH_2CH_2{}^+N(CH_3)_3$

2) <u>PG</u>:

3) <u>PA</u>: OH

4) <u>PE</u>: $OCH_2CH_2{}^+NH_3$

5) <u>PS</u>: $OCH(COO^-)(^+NH_3)$

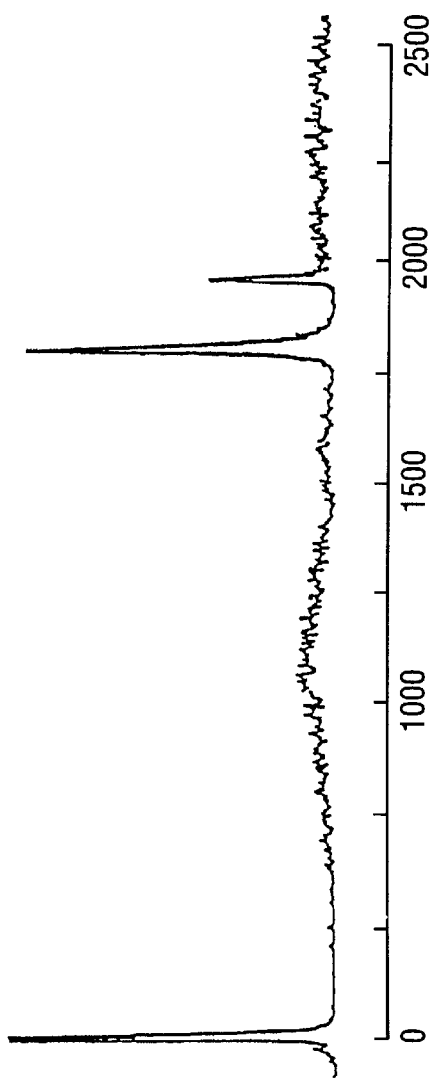
FIG. 4A
FIG. 4B
FIG. 4C

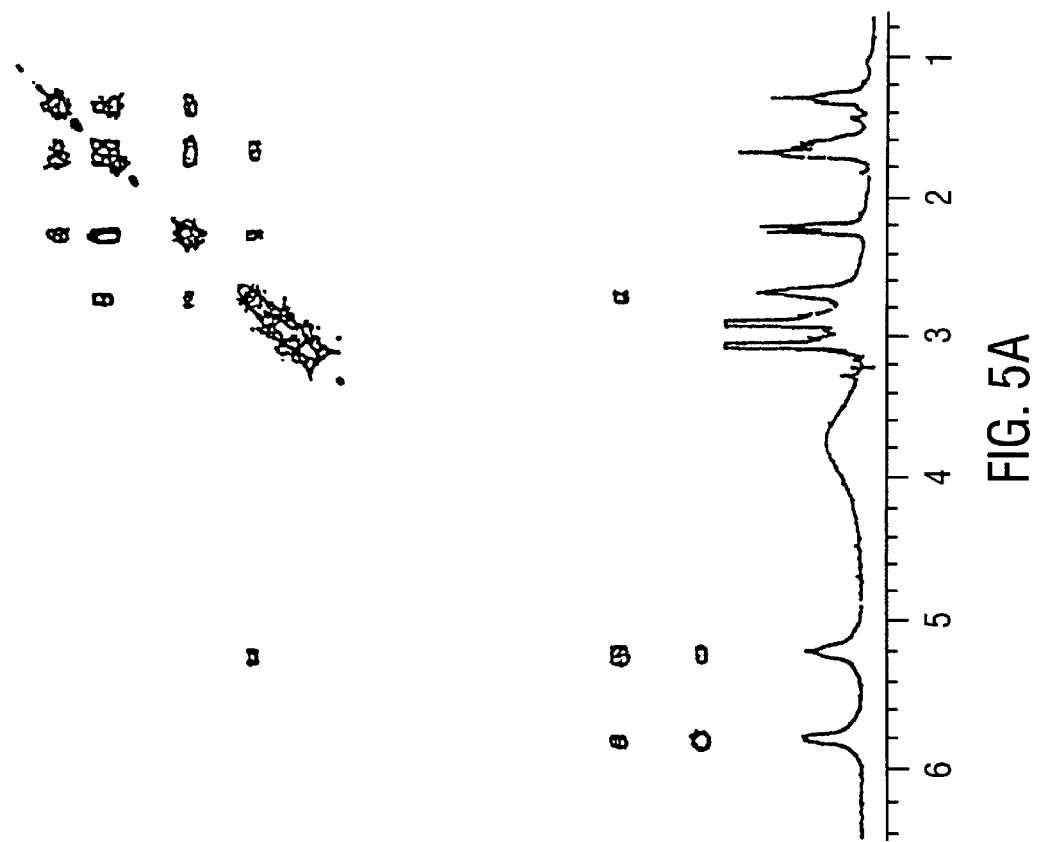

With lipids in dry powder

Mixing the lipids and NDDP
↓
Dissolving them in different solution 1) t-Butanol:water=10:1 → Sample 4
2) Methanol → Sample 5
3) Chloroform → Sample 6

Lyophilization for 1 d

Preliposomal NDDP powder

Reconstitution in saline (pH=6.5-7.0) → Sample 7

Reconstitution in saline (pH=3.0-4.0) → Sample 8

FIG. 6B

DELIVERY AND ACTIVATION THROUGH LIPOSOME INCORPORATION OF DIAMINOCYCLOHEXANE PLATINUM(II) COMPLEXES

This application is a division of U.S. Ser. No. 08/764,095 filed on Dec. 6, 1996 now U.S. Pat. No. 5,843,475.

BACKGROUND OF THE INVENTION

The present invention relates to methods and compositions for the treatment of cancer.

One drug that has proven effective in the treatment of certain tumors is cisplatin (cis-dichlorodiamine-platinum (II)). However, cisplatin has certain disadvantages. For example, its use in some circumstances is limited by its toxicity to the patient, especially its nephrotoxicity. As another example, tumors sometimes develop resistance to cisplatin.

In an effort to overcome the disadvantages of cisplatin, researchers have synthesized and tested various other platinum complexes as potential antitumor agents. One such compound is dichloro(1,2-diaminocyclohexane) platinum (II) (referred to in the remainder of this patent as "DACH—Pt—$Cl_2$"). However, this compound has very low solubility in water, making it impractical for formulation and administration in aqueous solution. Further, although various platinum complexes have been formulated in liposomes in the past, a liposomal formulation of DACH—Pt—$Cl_2$ has not been developed because that complex is insoluble in most organic solvents. Although it has good solubility in dimethylformamide, that solvent has a very high boiling point, therefore making it impossible or impractical to prepare a liposomal formulation of DACH—Pt—$Cl_2$ using standard evaporation methods.

Other platinum-based antitumor drugs, such as cis-bis-neodecanoato-trans-R,R-1,2-diaminocyclohexane platinum (II) (NDDP) have been prepared and tested as antitumor agents. However, a need still exists for improved antitumor drug formulations that have good antitumor activity, low toxicity to non-cancerous cells in a patient, and desirable storage characteristics.

SUMMARY OF THE INVENTION

The present invention relates to a liposomal antitumor composition and to methods of using the composition to inhibit tumor growth in mammals. The invention also concerns methods of preparing the antitumor composition.

The present invention can take advantage of intraliposomal conversion of a platinum complex having the formula

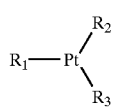

(I)

into a complex having the formula $R_1$—Pt—$X_2$ (II)

where X is halogen. This makes it possible to prepare liposomal formulations of the complex (II), which had not been practical previously due to its low solubility in water and most organic solvents.

In the above complexes, $R_1$ is diaminocycloalkyl, preferably a 1,2-diaminocycloalkyl group having from about 3 to about 6 carbon atoms, most preferably 1,2-diaminocyclohexane. $R_2$ and $R_3$ each have the formula

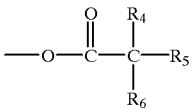

where $R_4$, $R_5$, and R6 are each independently hydrocarbon moieties having from 1 to about 10 carbon atoms, preferably alkyl having from 1 to about 6 carbon atoms, most preferably alkyl having from 1 to about 3 carbon atoms. $R_2$ and $R_3$ can be the same but do not have to be the same. Likewise, $R_4$, $R_5$, and $R_6$ can be the same but do not have to be the same. X is most preferably chlorine.

One aspect of the present invention is a liposomal antitumor composition that comprises the complex (II) entrapped in a liposome. In a particular embodiment of the invention, the liposome comprises an acidic phospholipid, for example dimyristoyl phosphatidyl glycerol. Without being bound by theory, it is believed that the presence of the acidic phospholipid in the liposome enhances or accelerates the conversion of the complex (I) to the complex (II).

Another aspect of the present invention is a method of inhibiting tumor growth. The method comprises administering to a mammal a composition that comprises the complex (II) entrapped in a liposome, with the platinum complex being present in an amount effective to inhibit tumor growth.

Another aspect of the present invention is a method of preparing the antitumor composition. This method comprises the step of adjusting the pH of a composition that comprises the platinum complex (I) entrapped in a liposome, whereby the pH is made somewhat acidic, preferably between about 2 and about 6.5, resulting in the conversion of the complex (I) into the complex (II). The resulting composition can then be administered to a patient.

In one particular embodiment of this method, the complex (I) is converted to the complex (II) within the liposome. This allows a liposomal formulation of the complex (I) to be manufactured and stored, and then shortly before administration to a patient, the liposomal formulation of complex (I) can be converted to a liposomal formulation of complex (II) in situ by simply adding an acidic solution to the formulation. Optionally, after a predetermined time has passed since the addition of the acidic solution, the pH can be readjusted, preferably to at least about 7, in order to stop the conversion of complex (I) to (II).

A broader aspect of the invention concerns a method of delivering a biologically active chemical moiety internally to a mammal. The biologically active moiety can be, for example, an antitumor agent. The method comprises (a) providing an aqueous formulation of a prodrug of the biologically active moiety, the prodrug being entrapped in a liposome, and the prodrug further being capable of forming the biologically active moiety upon exposure to a solution having an acidic pH; (b) reducing the pH to an acidic level, thereby converting the prodrug to the biologically active compound; and (c) administering the aqueous formulation to a mammal. Administration of the liposomal formulation to the mammal can suitably be done after the conversion of the prodrug, but it might also be done before conversion, such that the conversion would then occur in vivo, for example due to acidic components (e.g., acidic phospholipids) of the liposome.

The present invention has a number of advantages over prior art platinum antitumor formulations and methods, including better antitumor activity, greater potency, and reduced toxicity to non-cancerous cells of the patient. Further, the compositions of the present invention permit the formulation in liposomes and the delivery of platinum complexes that could not be so formulated in the past.

BRIEF DESCRIPTION OF THE DRAWINGS

FIG. 2. Effect of structure of Pt-complex, DMPG content, and aqueous solution on the intraliposomal stability and cytotoxicity of NDDP (✱), B10 (○), and L10 (■).

FIG. 4. $^{195}$Pt NMR of liposomal NDDP suspension. FIG. 4A—$^{195}$Pt NMR of Sample 1 in chloroform prepared by extraction with $CHCl_3$ from liposomal NDDP suspension reconstituted in saline and kept for 6 h at room temperature. FIG. 4B—$^{195}$Pt NMR of Sample 2 in $CH_3OH$ prepared by reconstitution of liposomal NDDP in saline for 6 h, lyophilization of water for 2 d, and redissolution of mixtures in $CH_3OH$. FIG. 4C—$^{195}$Pt NMR of Sample 3 in $CH_3OH$ prepared by evaporation of t-butanol and redissolution of mixtures in $CH_3OH$.

FIG. 5. FIG. 5A—$^1H$-$^1H$ correlated spectroscopy of DACH—Pt—$Cl_2$ in DMF-$d_7$.

FIG. 6. Sample preparation for NMR tracking experiment of liposomal NDDP. FIG. 6B—with lipids in dry powder.

DESCRIPTION OF SPECIFIC EMBODIMENTS

Figure 1:
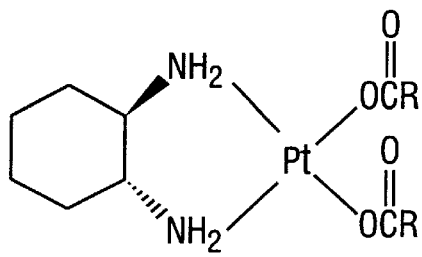
FIG. 1. Chemical structure of NDDP, B10, and L10.
Figure 1:
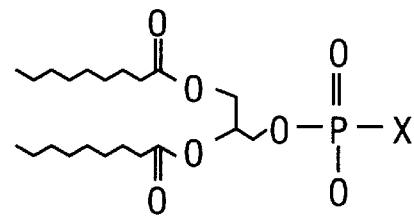
Figure 1:
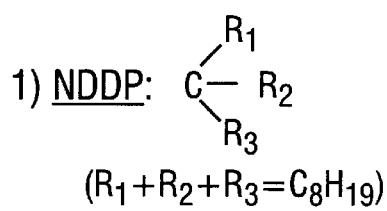
Figure 1:
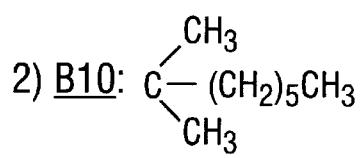
Figure 1:
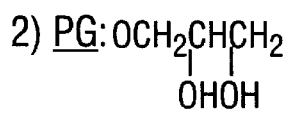
Figure 2A:
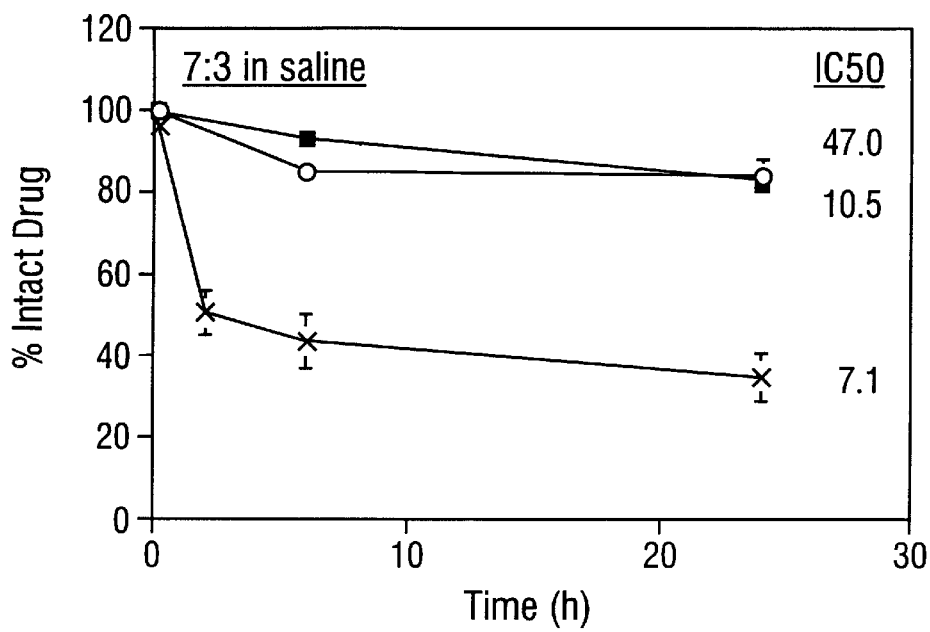
FIG. 2A—DMPC:DMPG=7:3, saline.
Figure 2B:
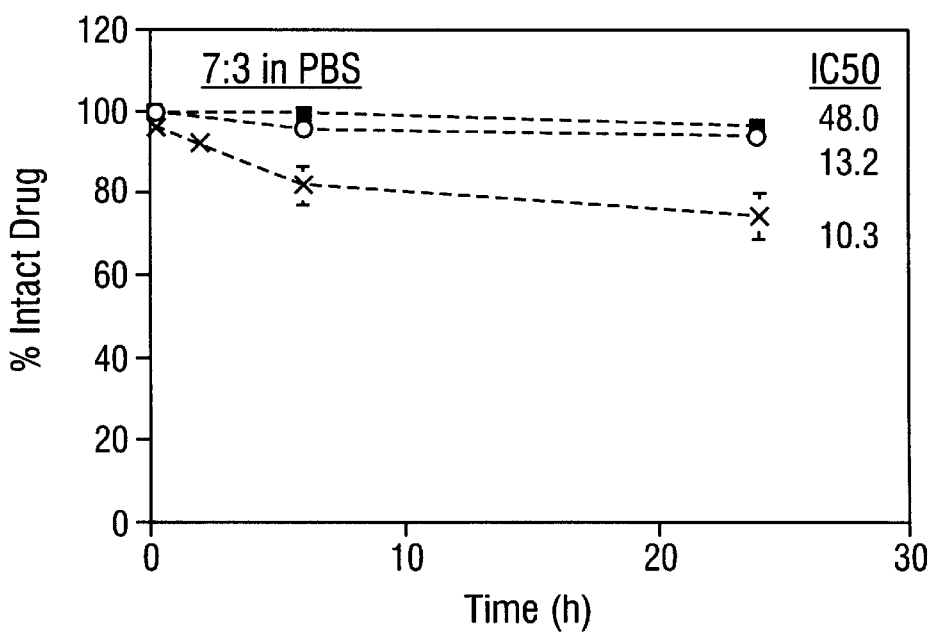
FIG. 2B—DMPC:DMPG=7:3, PBS.
Figure 2C:
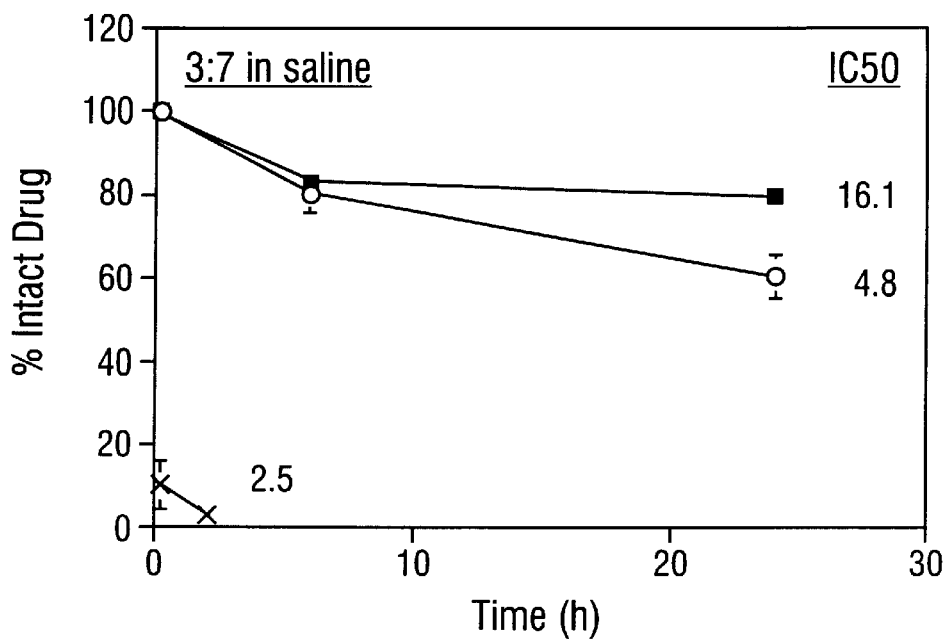
FIG. 2C—DMPC:DMPG=3:7, saline.
Figure 2D:
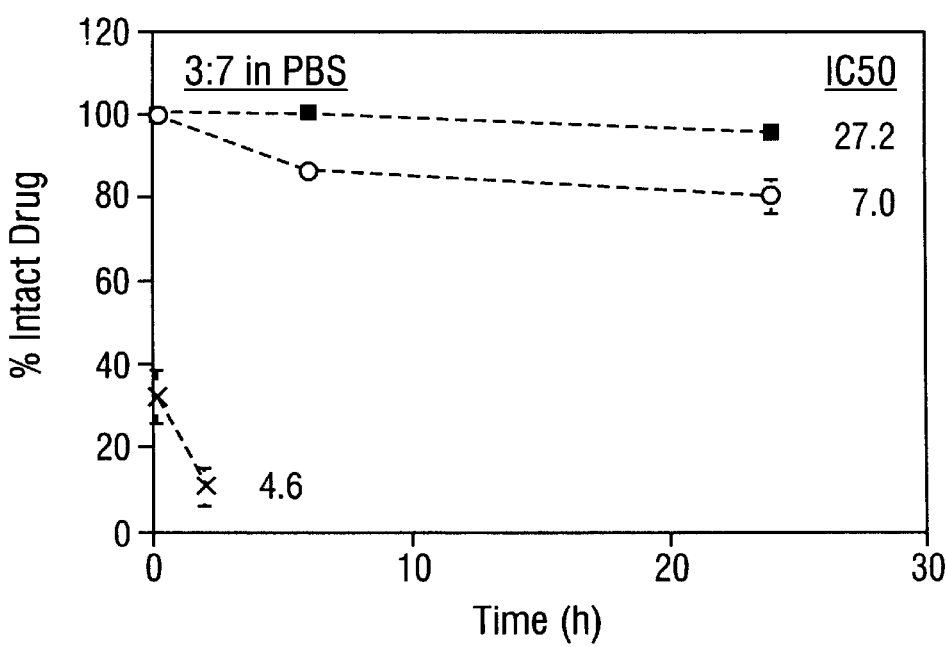
FIG. 2D—DMPC:DMPG=3:7, PBS. $IC_{50}$ values are in g/ml.

Cis-bis-neodecanoato-trans-R,R-1,2-diaminocyclohexane platinum (II) (NDDP) is a lipophilic platinum complex (Pt-complex) that can be formulated in a liposomal carrier. Various details about the making and use of NDDP and other platinum complexes are disclosed in U.S. Pat. Nos. 5,041,581, 5,117,022, 5,186,940, 5,178,876, and 5,384,127. Those patents are incorporated here by reference.

Prior studies have suggested that NDDP is a pro-drug that exerts its biological activity through activation within the liposome bilayers. In order to understand the kinetics of the intraliposomal degradation/activation of different liposomal Pt-complexes, we studied the effects that the structure of the Pt-complex, pH, temperature, lipid composition, content of acidic phospholipids, liposome size, and presence of residual chloroform have on the stability, in vitro cytotoxicity, and in vivo antitumor activity of different liposomal Pt-complex preparations. The following factors were found to enhance the intraliposomal degradation/activation of Pt-complexes: 1) the size and spatial configuration of the Pt-complex, 2) an acidic pH, 3) a high temperature, 4) the presence and amount of acidic phospholipids, and 5) the presence of residual chloroform. Liposome size did not affect the intraliposomal stability of different Pt-complexes.

A good inverse relationship between the extent of drug degradation and in vitro cytotoxicity and between the extent of drug degradation and in vivo antitumor potency was observed, thus confirming that the biological activity of these complexes is exerted through the intraliposomal formation of certain active intermediate(s). The only active intermediate that could be identified was cis-bis-dichloro-trans-R,R-1,2-diaminocyclohexane platinum (II) whose structure was confirmed by $^1H$, $^{13}C$, and $^{195}Pt$ nuclear magnetic resonance EMR) spectroscopy.

We have previously developed liposomal formulations of lipophilic Pt-complexes for in vivo administration [5,6] and have studied their chemical and biological properties. [1,4,7] The general structure of the preferred Pt-complexes used is [DACH—Pt—$R_2$], where DACH is trans-R,R-1,2-diaminocyclohexane and R is a lipophilic carboxylato group. The Pt-complex is thought to intercalate between the phospholipid molecules of the lipid bilayers of the liposomes. The most remarkable characteristic of these complexes is that they are not cross-resistant with cisplatin, both in vitro and in vivo. [1,5] The leading formulation, liposomal cis-bis-neodecanoato-DACH-platinum (II) (NDDP) uses large liposomes composed of dimyristoylphosphatidyl choline (DMPC) and dimyristoylphosphatidyl glycerol (DMPG) at a 7:3 molar ratio and is now in clinical trials. Interestingly, liposomal-NDDP must undergo a chemical degradation/activation process into an active intermediate(s) within the liposomes shortly after liposome preparation in order to exert its antitumor activity. [7] We have previously reported that this chemical reaction depends on the content of DMPG in the lipid bilayer, and based on this finding, we hypothesized that a DMPG-Pt complex might be one of the active intermediates. We have also reported that the structure of the Pt-complex has an effect on the intraliposomal drug stability: the compounds with linear and short carboxylato leaving groups are more stable and less potent than the compounds with branched or longer linear leaving groups. [8] A full characterization of the active intermediate(s) as well as the different factors that influence the degradation/activation process is mandatory for the development of one of these agents as a pharmaceutical product.

For that purpose, we selected NDDP (highly branched structure) and two isomers, B10 (minimally branched structure) and L10 (linear structure) (FIG. 1) and studied the relationship between their biological activity and their intraliposomal stability. We examined the effect of pH, temperature, lipid composition, liposome size, and presence of residual chloroform on the degradation of the Pt-complexes, and attempted to identify the active intermediate(s) by tracking experiments using $^{31}P$ and $^{195}Pt$ NMR spectra. Our results indicate that the degradation/activation of these Pt-complexes is greatly dependent on the pH of the suspension, and that DACH-dichloroplatinum (DACH—Pt—$Cl_2$) is the only intermediate that can be identified, thus suggesting that these Pt-complexes are pro-drugs of DACH—Pt—$Cl_2$ when incorporated in liposomes suspended in saline.

MATERIALS AND METHODS

Preparation of Liposomal Pt-complex

NDDP, B10, and L10 were synthesized as previously described [1,2] and recrystallized in acetone. DMPC, DMPG, dioleyl phosphatidyl choline (DOPC), dioleyl phosphatidyl glycerol (DOPG), phosphatidic acid (PA), phosphatidyl ethanolamine (PE), and phosphatidyl serine (PS) were purchased from Avanti Polar Lipids (Alabaster, Ala.).

Multilamellar vesicles containing Pt-complexes were prepared by the lyophilization method using the lipids in chloroform solutions or in dry powder.

Method 1: With chloroform solutions of lipids [1], lipids were mixed at the desired molar ratio, and the chloroform was removed in a rotary evaporator. To the dried lipid film, t-butanol solutions of Pt-complex were added and shaken at 40° C. for 10 min. The solutions were then frozen in a dry-ice-acetone bath, and t-butanol was removed by lyophilization overnight to give lyophilized preliposomal powder.

Method 2: With lipids in dry powder, lipids were mixed and dissolved in t-butanol:water (10:1/v:v). To this solution, t-butanol solutions of Pt-complex were added, and the rest of the procedure was the same as described above.

Saline or PBS was added (1 ml/mg of Pt-complex) to reconstitute the lyophilized preliposomal powder, and the suspension was hand-shaken for 10 min to obtain large-size liposomes. Small-size liposomes were prepared by sonication of large-size liposomes for 1 min with an ultrasonic cell disrupter (Laboratory Supplies Co., New York, N.Y.). The size distribution of the different liposomal preparations was determined with a Nicomp Submicron Particle Sizer Model 370 (Nicomp Particle Sizing Systems, Santa Barbara, Calif.).

Intraliposomal Stability

Stability of the different Pt-complexes incorporated in liposomes was determined as described previously [8] by comparing the HPLC profiles as a function of time. In brief, aliquoted samples of liposome suspension were diluted (7×) with methanol at 0, 2, 6, and 24 h after liposome preparation, and each sample was then monitored by HPLC using chromega-8 bond column (4.6 mm×25 cm, 8 µm: ES Industries, N.J.) and 10% water-methanol as eluant. The flow rate was 1 ml/min, and the complexes were detected by UV at 224 nm wavelength.

Biological Activity

In vitro. The in vitro cytotoxicity of liposomal Pt-complexes against A2780 human ovarian carcinoma cells was assessed by the MTT dye reduction assay. In brief, A2780 cells were seeded in 96-well plates, allowed to attach overnight, and then exposed to various concentrations of drugs for 20 h. After washing the cells with PBS, fresh medium was added for 52 hours and the cell survival fractions determined by MTT assay.

In vivo. The in vivo antitumor activity of liposomal Pt-complexes was assessed against intraperitoneal L1210 mouse leukemia. Groups of 6–8 mice weighing 18–20 g were inoculated with 106 cells (0.2 ml, i.p.) on day 0, and treatment (25, 50, 100 and 150 mg/kg) was started on day 1 (0.15–0.5 ml, i.p.). The results were expressed as the median survival of treated animals divided by the median survival of control animals×100 (% T/C).

Identification of Active Intermediates

To characterize the active intermediate(s) in the reaction cascade of L-NDDP reconstituted in saline (0.9% NaCl), tracking experiments using $^{195}$Pt NMR spectra in combination with $^{31}$P NMR were performed. The procedures for the preparation of the samples is summarized in FIG. 6. Samples 1–3 were prepared using the lipids DMPC and DMPG purchased in chloroform solution, while samples 4–8 were prepared using lipids in dry powder. In samples 1–3, the chloroform was initially evaporated in a rotavapor. The lipid film was dissolved in t-butanol containing the NDDP in solution. An aliquot of this solution was kept at 40° C. for 6 h and then lyophilized and extracted with methanol (sample 3). The remaining was lyophilized immediately, thus resulting in a preliposomal powder, which was reconstituted with saline to produce the liposome suspension. The liposome suspension was kept at room temperature for 6 hours. The Pt compounds and lipids were then extracted with chloroform (sample 1) or the sample was lyophilized to eliminate the water and the powder dissolved in methanol (sample 2) (see FIG. 6). Samples 4, 5, and 6 were prepared by complete evaporation of solvents after keeping the samples at 40° C. for 6 h, and redissolving them in methanol. Samples 7 and 8 were prepared by lyophilization of water for 1–2 d and redissolution in methanol. All samples were prechecked by HPLC before tracking with NMR. Chemical shifts of the products are expressed in parts-per-million relative to $Na_2PtCl_6$ in $^{195}$Pt and DMPC in $^{31}$P NMR.

DACH—Pt—Cl$_2$ Characterization

Yellow precipitates from NMR samples were collected and redissolved in DMF-d$_7$ to characterize them with $^1$H and $^{13}$C NMR. $^1$H NMR (DMF-d$_7$): 1.13–1.17 (m, 2H), 1.46–1.55 (m, 4H), 2.05–2.09 (broad, 2H) 2.55–2.59 (m, 2H), and 5.07 and 5.63 (broad s, 2 NH2) ppm. $^{13}$C NMR (DMF-d7): 24.9 (C4, C5), 32.3 (C3, C6), and 64.1 (C1, C2) ppm. $^{195}$Pt NMR (CHCl$_3$, CH$_3$OH) 1950 ppm, (DMF) 2250 ppm (strong single peak). Elemental analysis: Calc. C(18.99), H(3.69), N(7.38), Pt(51.50); Found C(18.58), H(3.72), N(7.40), Pt(51.30). All these data were confirmed by an authentic sample of DACH—Pt—Cl$_2$.

RESULTS

Preparation of Liposomal Pt-complexes

NDDP and its two isomers, B10 and L10 were formulated in liposomes composed of combinations of various lipids including DMPC, DMPG, DOPC, DOPG, PA, PE, and PS. The liposomes were formed by reconstituting preliposomal powders containing the Pt-complex and the lipids with unbuffered 0.9% NaCl aqueous solution (saline) or phosphate-buffered saline (PBS). The entrapment efficiency (%EE) of all liposomal formulations was >90% and was not significantly affected by the lipid composition, reconstitution solution, or NDDP isomer used. No crystals of free drug were observed in any of these preparations within 24 h as assessed by optic microscopy. The median size of the multilamellar vesicles was 1–2 µm in all preparations. The median size of the small-size liposomes prepared by ultrasonication of multilamellar vesicles was 50–100 nm.

Intraliposomal Stability of Pt-complexes

1) Role of the spatial configuration of the Pt-complex and pH of the liposome suspension.

FIGS. 2A–D show the stability of liposomal Pt-complex formulations using saline or PBS as the reconstitution solution and DMPC:DMPG ratios of 7:3 and 3:7. As observed previously [1], the branched configuration of the leaving group of the Pt-complex and the content of DMPG in the lipid bilayers correlated with a higher rate of degradation of the Pt-complex. As a result, the complex with a linear leaving group L10 was highly stable, while the highly branched NDDP was rather unstable, and the minimally branched B10 had an intermediate stability. The use of PBS as the reconstitution solution resulted in a significantly higher stability of the Pt-complexes as compared with saline. For example, 6 h after liposome preparation, the percentages of intact NDDP in saline versus PBS were 43.7% vs 82.1%, whereas the percentages for B10 were 85.0% vs 95.9%, and the percentages for L10 93.1% vs 100%, respectively. The pH of the liposome suspension in saline decreased from 7.0 to 3.8–6.2 depending on the Pt-complex, whereas PBS held the pH of the solution to around 6.0–7.0 in all cases. These results indicate that: 1) an acidic pH enhances the intraliposomal degradation of the Pt-complexes, and 2) a good neutral buffer system can reduce or stop the intraliposomal degradation of the Pt-complexes. To confirm these results, we tested the intraliposomal stability of the Pt-complexes in strongly acidic (pH=3.0) or basic (pH=8.0) saline solutions prepared by adding 0.1 N HCl or NaOH aqueous solution to pH 7.0 saline. The pH 3.0 saline increased the degradation rate of all Pt-complexes, whereas the pH 8.0 saline did not induce any significant Pt-complex degradation even at 24 h after liposome preparation. All formulations using a relative higher amount of DMPG (DMPC:DMPG=3:7) displayed a higher rate of Pt-complex degradation in good correlation with the pH of the liposome suspension, because DMPG is an acidic phospholipid.

2) Role of Temperature

The intraliposomal stability of the Pt-complexes was checked at 40° C. and compared with results obtained at room temperature. Pt-complex degradation was temperature-dependent, with the degradation rates being about 30–70% higher at 40° C. than at 25° C., depending on the Pt-complex tested.

3) Role of Lipid Composition

Figure 3:
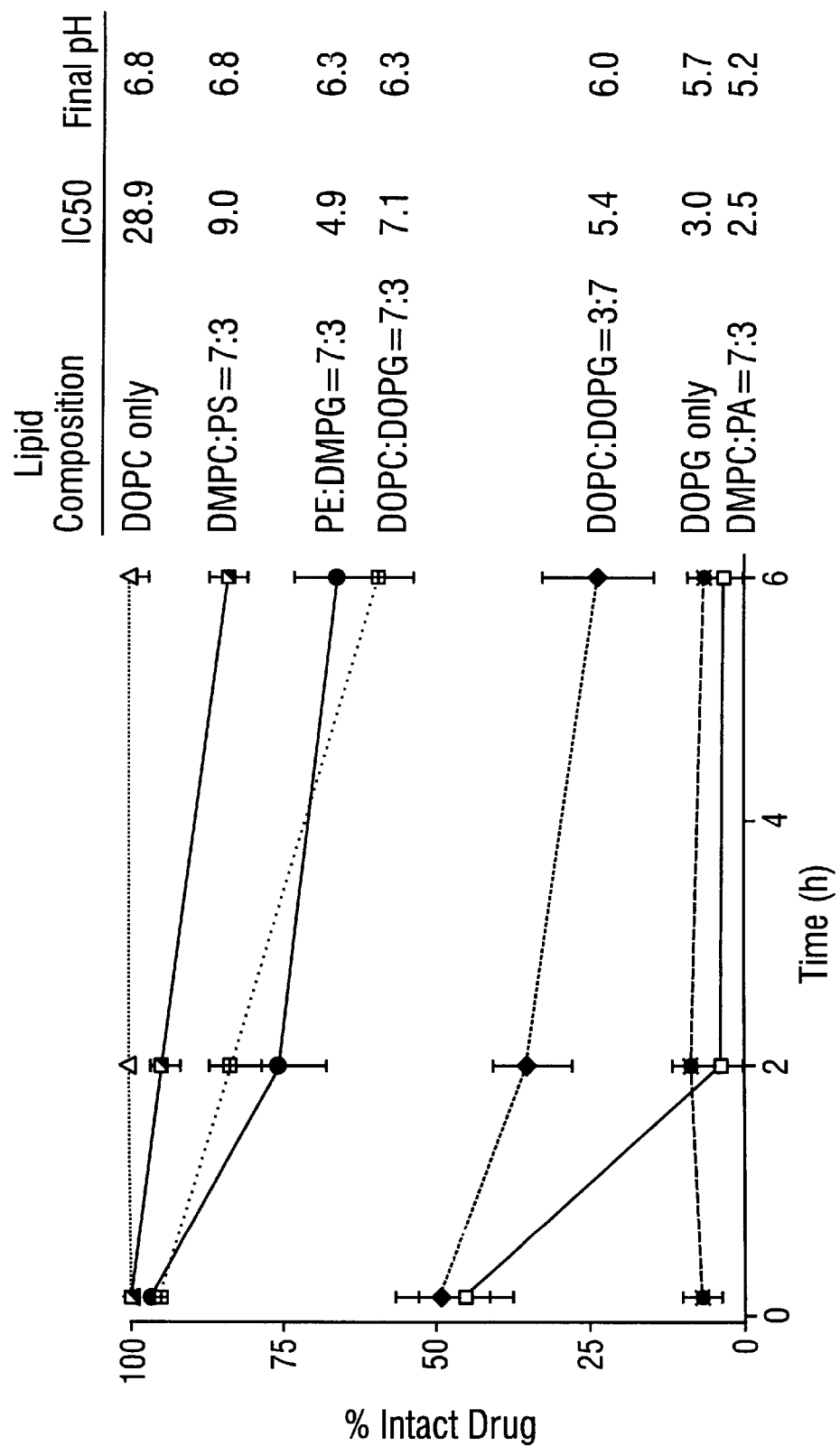
FIG. 3. Effect of lipid composition on the intraliposomal stability of NDDP. 0.9% NaCl aqueous solution (starting pH=7.0) was used as reconstituting solution of liposomes and the final pH was checked at 6 h after liposome preparation.

Liposomal formulations of NDDP using DMPC:PA, PS:DMPG, and DMPC:PE at a 7:3 molar ratio, and DOPC:DOPG at 1:0, 7:3, 3:7, and 0:1 molar ratios were prepared and tested using saline as the reconstitution solution (FIG. 3). The acidity of phospholipids (PA>PG>PS) and the relative DOPG content (DOPC:DOPG 0:1>3:7>7:3>1:0) enhanced the intraliposomal degradation of NDDP and a good correlation between Pt-complex degradation and acidic pH was again observed.

The same conclusion was drawn in studies with NDDP in liposomes with the same DMPC:DMPG molar ratio (7:3) but different NDDP:total lipid ratios (1:5, 1:10, 1:15, and 1:30) and, therefore, different DMPG contents. Using a 1:5 or 1:10 ratio, 85% of initial NDDP was present at 24 hours; in contrast, using a 1:15 or 1:30 ratio resulted in an enhanced NDDP degradation, with only 25% of the original NDDP remaining at 24 h, thus suggesting a correlation between extent of degradation and absolute amount of DMPG within the lipid bilayers.

4) Role of Liposome Size

Liposome size did not affect the intraliposomal stability of NDDP: ultrasonication of the original suspension of multilamellar vesicles did not significantly change the stability of NDDP regardless of the lipid composition used.

Correlation Between In Vitro Cytotoxicity and Intraliposomal Stability

We studied the in vitro cytotoxicity of different liposomal Pt-complex preparations against A2780 cells with the MTT assay and correlated the results with the intraliposomal stability of the Pt-complex. Results are shown in FIGS. 2A–D. The $IC_{50}$ values correlated fairly well with drug stability: the more stable the Pt-complex, the less toxic or higher the $IC_{50}$. When about 20%, 50%, and 90% of the original Pt-complex remained at 6 h, the $IC_{50}$ was approximately 3–5, 7–10, and 20–50 g/ml, respectively. These results indicate that the intraliposomal degradation of the Pt-complex is required to exert its cytotoxic effect and is, therefore, an intraliposomal activation step.

Identification of Active Intermediate(s) of NDDP

No new peaks corresponding to the degradation products are observed by the HPLC method developed for NDDP, either because they elute with the phospholipids or they do not have UV absorbence. Attempts to separate any new peaks from the lipid peaks have been so far unsuccessful.

To keep track of the reaction cascade of liposomal NDDP, we tried to apply the NMR tracking technique used by other researchers [2, 3, 9–11] to characterize the degraded/activated products of NDDP.

Figure 6A:
FIG. 6A—with lipids in chloroform solutions.

1) Formulations prepared using lipids in chloroform solution (samples 1, 2, and 3 of FIG. 6A).

By $^{195}$Pt NMR of sample 1 (saline, chloroform extraction, FIG. 4A) and sample 2 (saline, lyophilization, FIG. 4B), the NDDP peak was detected at 1750 ppm and a new peak corresponding to DACH—Pt—$Cl_2$ was detected at 1950 ppm. Prolonging the reaction time, lowering the pH, increasing the temperature, and increasing the amount of DMPG in the liposomes enhanced the degradation/activation of NDDP, increasing the intensity of the peak at $^{195}$0 ppm. However, by $^{31}$P NMR, no new peaks were observed except those corresponding to DMPC (2 ppm) and DMPG (3 ppm), indicating that the new product shown by $^{195}$Pt NMR is not a DMPG-incorporating Pt-complex.

Figure 5B:
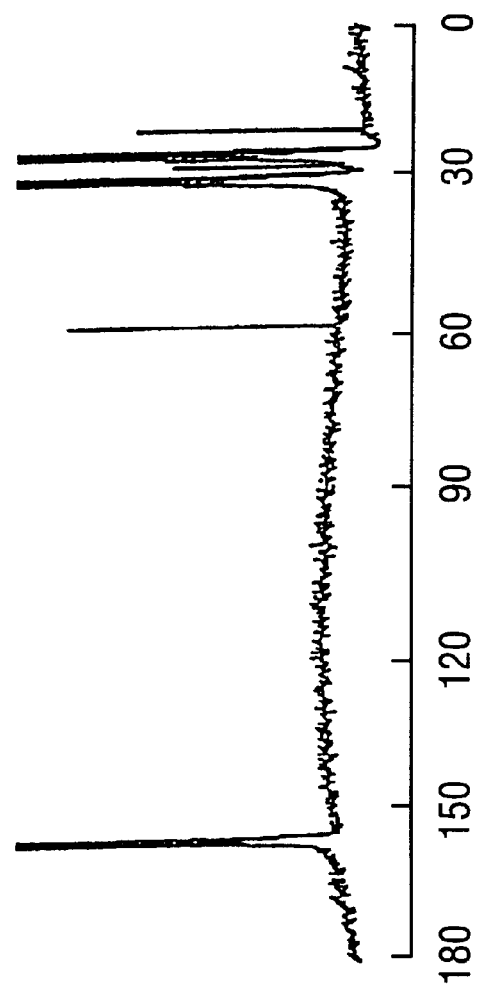
FIG. 5B—$^{13}C$ NMR of DACH—Pt—$Cl_2$ in DMF-$d_7$.

These spectra results were similar to those from sample 3 (FIG. 6A, t-butanol, lyophilization, FIG. 4C), in which liposomal NDDP was not exposed to saline, thus indicating that the presence of $CHCl_3$ can also act as a donor of chloride to form DACH—Pt—$Cl_2$. After storing the yellowish NMR samples at 4° C. overnight, yellow crystals slowly precipitated. The precipitates were filtered, dried, and the structure of the compound was proved to be DACH—Pt—$Cl_2$ by $^1$H, COSY (FIG. 5A), $^{13}$C (FIG. 5B), and $^{195}$Pt NMR. A yellow precipitate was also observed 2–3 weeks after leaving the original liposomal NDDP suspension at room temperature. NDDP in liposomes composed of only DMPC did not give any new peaks by either $^{195}$Pt or $^{31}$P NMR, which correlates with its completely preserved stability in the absence of DMPG.

2) Formulations prepared using lipids in dry powder (samples 4, 5, 6, 7, and 8).

We performed the same tracking experiment with formulations prepared using lipids in dry powder instead of chloroform solutions to eliminate the influence of the presence of residual $CHCl_3$ on the degradation of NDDP (FIG. 6). In samples 4 and 5 (solvent t-Butanol+water and methanol, respectively) containing lipids and NDDP, no reactions occurred, whereas sample 6 (chloroform solution of lipids and NDDP) showed the presence of DACH—Pt—$Cl_2$ by $^{195}$Pt NMR. The results with these samples, which were incubated at 40° C. for 6 h, confirm that the presence of chloroform can induce the degradation of NDDP into DACH—Pt—$Cl_2$. Sample 7 was prepared by reconstitution of preliposomal NDDP powder in saline of pH 6.5–7.0 for 6 h at room temperature. No significant degradation (<5%) was observed, whereas when reconstituted in acidic saline of pH 3.0–4.0 (sample 8), a 60–95% degradation of NDDP occurred in 10 min yielding DACH—Pt—$Cl_2$ as determined by $^{195}$Pt NMR and HPLC (Table 1).

TABLE 1

Effect of various pH values of saline on intraliposomal stability of NDDP prepared with lipids as dry powder.

| pH of saline | NDDP stability (%) Time after reconstitution | | | |
|---|---|---|---|---|
| | 10 min | 1 h | 2 h | 6 h |
| 3.0 | 43 | — | 15 | 7 |
| 5.0 | 80 | 72 | 67 | 38 |
| 7.0 | 100 | — | 95 | 92 |

Relationship Between Pt-complex Stability and In Vivo Antitumor Activity

1. Preparations Containing Residual Chloroform

These studies were done with liposomal Pt-complex suspensions prepared using lipids dissolved in chloroform. In in vivo antitumor activity studies against L1210 leukemia, an inverse relationship between drug stability and antitumor potency was observed (Table 2). The DMPC:DMPG ratio was 7:3 for all preparations. The starting pH value of the saline and PBS was 7.0. The tumors were inoculated i.p. on day 0, followed by drug injection i.p. on day 1.

TABLE 2

In vivo antitumor activity of liposomal Pt complexes against L 1210 leukemia.

| Pt complex | Dose of Pt complex (mg/kg) | % T/C Reconstitution solution | |
|---|---|---|---|
| | | Saline | PBS |
| NDDP | 25 | 157 | 114 |
| | 50 | 211 | 171 |
| | 100 | Toxic | 200 |
| | 150 | Toxic | 150 |
| B10 | 25 | 114 | 114 |
| | 50 | 128 | 114 |
| | 100 | 228 | 142 |
| | 150 | 163 | 163 |
| L10 | 25 | 100 | 114 |
| | 50 | 157 | 100 |
| | 100 | 178 | 100 |
| | 150 | 123 | 100 |
| Cisplatin | 10 | 142 | |

The optimal doses of liposomal NDDP were 50 mg/kg in saline and 100 mg/kg in PBS (%T/C=211 and 200, respectively). For liposomal B10 and L10, the optimal dose was 100 mg in saline (%T/C=228 and 178), but no significant antitumor activity was obeserved when both drugs were reconstituted in PBS. In conclusion, the most potent liposomal Pt-complex preparations are those with the lowest stability of the Pt-complex. However, all formulations had similar antitumor activity when administered at the optimal dose.

2. Preparations Not Containing Residual Chloroform

These studies were done with liposomal Pt-complex suspensions prepared with dry. The relationship between NDDP stability and antitumor activity was again studies using the in vivo L1210 leukemia model. Table 3 shows the results with formulations reconstituted with saline solutions of different pH and administered at different time points after reconstitutedion. (Values are the means of two separate experiments.)

TABLE 3

Antitumor activity of liposomal NDDP against L 1210 leukemia.

| Drug | pH of saline | Dose of Pt complex (mg/kg) | % T/C Time of drug administration | | |
|---|---|---|---|---|---|
| | | | 10 mm | 2 h | 6 h |
| NDDP | 3.0 | 12.5 | | | 157 |
| | | 25 | 150 | 186 | 240 |
| | | 50 | | | Toxic |
| NDDP | 5.0 | 12.5 | | | 186 |
| | | 25 | | | 200 |
| | | 50 | 133 | 216 | 270 |
| | | 100 | | | Toxic |
| NDDP | 7.0 | 25 | | | 186 |
| | | 50 | | | 200 |
| | | 100 | 163 | 216 | 257 |
| Cisplatin | | 10 | | | 150 |

The optimal doses of liposomal NDDP reconstituted with salines of pH 3.0, 5.0, and 7.0 were 25, 50, and 100 mg/kg, respectively. Therefore, the lower the pH, the higher the potency of the preparation in good correlation with the increased intraliposomal drug degradation/activation. At the optimal doses, the %T/C obtained were 214, 271, and 271, respectively. Delaying the time of drug administration increased the antitumor activity of the formulations, in good correlation with the increased drug activation with time. However, antitumor activity did not correlate perfectly with the calculated amount of activated Pt-species formed intraliposomally during the activation process. For example, 100 mg/kg at pH 7.0 gave a similar %T/C value as 50 mg/kg at pH 5.0, although only 10% of NDDP at pH 7.0 (10 mg/kg) and about 70% at pH 5.0 (35 mg/kg) are transformed into the active Pt-species under those conditions. Further in vivo activation must, therefore, occur to explain these discrepancies.

DISCUSSION

Our results indicate that NDDP and its isomers are prodrugs of DACH—Pt—$Cl_2$ when entrapped in liposomes containing acidic phospholipids and in the presence of sodium chloride or residual chloroform as donors of chloride. The rate of transformation of NDDP into DACH—Pt—$Cl_2$ is directly related to the pH of the liposome suspension. The studies performed suggest that DMPG and other acidic phospholipids enhance the reaction by providing an acidic milieu within the liposome membranes. No evidence could be generated to support a direct reaction between NDDP and DMPG to form a DACH—Pt—DMPG complex as one of the active intermediates of NDDP, as we had previously hypothesized, nor the formation of DACH—Pt aquated species.

DACH—Pt—$Cl_2$ is the leading compound of the DACH family of Pt-complexes. However, it was never developed because of a lack of solubility in water. We initially considered this compound for liposome entrapment but determined it to be an inappropriate drug for liposome formulation because it is insoluble in most organic solvents. DACH—Pt—$Cl_2$ has only a good solubility in dimethylformamide (DMF), which has a very high boiling point and, therefore, can not be used to prepare liposomes using the standard evaporation methods and it is not soluble in any of the organic solvents used for the lyophilization methods. Our studies indicate that DACH—Pt—$Cl_2$ can be generated within the liposome membranes under the conditions described and that the drug remains liposome-bound without leaking out and crystallizing for at least 24 h. In contrast, DACH—Pt—$Cl_2$ precipitates quickly when formed from NDDP by the addition of HCl. These results constitute the first example of a liposome formulation in which the compound is synthesized in situ from an entrapped precursor and the liposomes prevent its spontaneous precipitation. The results are encouraging because they may suggest an avenue for the development of a much needed delivery system for this very interesting compound.

A potential strategy is to use a two-step reconstitution procedure by which an acidic saline solution is used first to induce the fast transformation of >80% of NDDP into DACH—Pt—$Cl_2$, followed after a predetermined period of time by the addition of a buffer solution to bring the pH to >7.0 and to stop the reaction.

Liposomes in accordance with the present invention can be prepared from various amphipathic substances including natural or synthetic phospholipids. Numerous suitable phospholipids are well known in the art. The liposomes of the present invention can be multilamellar, unilamellar, or have an undefined lamellar construction. A pharmaceutical composition comprising such liposomes can include a pharmaceutically acceptable carrier or diluent, as well as other pharmaceutically acceptable adjuvants.

Liposome compositions of the present invention can be used to inhibit the growth of tumor cells in mammals, particularly in humans. The compositions of the present invention should be useful for treatment of various human malignancies, in particular any platinum-sensitive cancer, including ovarian, testicular, lung, head and neck, esophageal, and bladder tumors, sarcomas, lymphomas, and mesotheliomas. Methods of using the compositions of the present invention involve administering to a mammal an amount of the compositions effective to inhibit tumor growth. The administering step can suitably be parenteral and by intravenous, intraarterial, intramuscular, intralymphatic, intraperitoneal, subcutaneous, intrapleural, or intrathecal injection, or by topical application or oral dosage. Such administration is preferably repeated on a timed schedule until tumor regression or disappearance has been achieved, and may be used in conjunction with other forms of tumor therapy such as surgery or chemotherapy with different agents. The dose administered of a composition in accordance with the present invention is preferably between approximately 100 and 750 mg/kg of body weight of the mammalian subject to which it is administered.

The preceding description of specific embodiments of the present invention is not intended to be a complete list of every possible embodiment of the invention. Persons skilled in this field will recognize that modifications can be made to the specific embodiments described here that would be within the scope of the present invention.

REFERENCES

The following references, to the extent that they provide exemplary procedural or other details supplementary to those set forth herein, are specifically incorporated herein by reference.

1. Han, I.; ling, Y.-H.; Al-Baker, S.; Khokhar, A. R.; Perez-Soler, R. Cellular pharmacology of liposomal cis-bis-neodecanoato-trans-R,R-1,2-diaminocyclohexane-platinum(II) in A2780/S and A2780/PDD cells. Cancer Res. 1993, 53, 4913–4919.
2. Hollis, L. S.; Miller, A. V.; Amundsen, A. R.; Schurig, J. E.; Stem, E. W. cis-Diamineplatinum(II) complexes containing phosphono carboxylate ligands as antitumor agents. J. Med. Chem. 1990, 33, 105–111.
3. Ismail, I. M.; Sadler, P. J. $^{195}$Pt- and $^{15}$N-NMR studies of antitumor complexes. In: Platinum, gold, and other metal chemotherapeutic agents; Lippard, S. J. (eds.) American Chemical Society. 1983; pp 171–189.
4. Khokhar, A. R.; Al-Baker, S.; Brown, T.; Perez-Soler, R. Chemical and biological studies on a series of lipid-soluble (trans-(R,R)- and -(S,S)-1,2-diaminocyclohexane)platinum(II). J. Med. Chem. 1991, 34,325–329.
5. Perez-Soler, R.; Yang, L. Y.; Drewinko, B.; Lauterzstain, J.; Khokhar, A. R. Increased cytotoxicity and reversal of resistance of cis-diamminedichloro platinum(II) with entrapment of cis-bis-neodecanoato-trans-R,R-1,2-diaminocyclohexaneplatinum(II) in multilamellar lipid vesicles. Cancer Res. 1988, 48, 4509–4512.
6. Perez-Soler, R.; Khokhar, A. R.; Lautersztain, J.; Al-Baker, S.; Francis, K.; Macias-Kiger, D.; Lopez-Berestein, B. Clinical development of liposomal platinum. J. Liposome Res. 1990, 1, 437–449.
7. Perez-Soler, R.; Khokhar, A. R. Lipophilic cisplatin analogues entrapped in liposomes: role of intraliposomal drug activation in biological activity. Cancer Res. 1992, 52, 6341–6347.
8. Perez-Soler, R.; Han, I.; Al-Baker, S.; Khokhar, A. R. Lipophilic platinum complexes entrapped in liposomes: improved stability and preserved antitumor activity with complexes containing linear alkyl carboxylato leaving groups.
Cancer Chemother. Pharmacol. 1994,33,378–384.
9. Qu, Y.; Farrell, N. J. Effect of diamine linker on the chemistry of bis(platinum) complexes. A comparison of the aqueous solution behavior of 1,4-butanediamine and 2,5-dimethyl-2,5-hexanediamine complexes. J. Inorg. Biochem. 1990, 40, 255–264.
10. Qu, Y.; Farrell, N. J. Interaction of bis(platinum) complexes with the mononucleotide 5'-guanosine monophosphate. Effect of diamine linker and the nature of the bis(platinum) complex on product formation. J. Am. Chem. Soc. 1991, 113, 4851–4857.
11. Slavin, L. L.; Bose, R. N. Phosphonato complexes of platinum(II): kinetics of formation and phosphorus-31 NMR characterization studies. J. Inorg. Biochem. 1990, 40, 339–347.

We claim:

1. A liposomal antitumor composition, comprising a platinum complex having the formula

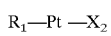

entrapped in a liposome, where the liposome comprises dioleyl phosphatidyl glycerol, and where $R_1$ is diaminocycloalkyl and X is halogen.

2. The composition of claim 1, where $R_1$ has from 3 to 6 carbon atoms.

3. The composition of claim 1, where $R_1$ is 1,2-diaminocyclohexane.

4. The composition of any one of claims 1–3, where X is chlorine.

5. The composition of claim 1, where the liposome further comprises dioleyl phosphatidyl choline.

6. The composition of claim 1, where the platinum complex is intercalated between the bilayers of the liposome.

7. A liposomal antitumor composition, comprising a platinum complex having the formula

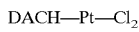

intercalated between the bilayers of a liposome, where the liposome comprises dioleyl phosphatidyl glycerol, and where DACH is diaminocyclohexane.

8. A method of inhibiting tumor growth, the method comprising administering to a mammal a composition, in an amount effective to inhibit tumor growth, the composition comprising a platinum complex having the formula

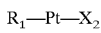

entrapped in a liposome, where the liposome comprises dioleyl phosphatidyl glycerol, and where $R_1$ is diaminocycloalkyl and X is halogen.

9. The method of claim 8, where $R_1$ has from 3 to 6 carbon atoms.

10. The method of claim 8, where $R_1$ is 1,2-diaminocyclohexane.

11. The method of any one of claims 8–10, where X is chlorine.

12. The method of claim 8, where the liposome further comprises dioleyl phosphatidyl choline.

13. The method of claim 8, where the complex is intercalated between bilayers of the liposome.

14. A method of inhibiting tumor growth, the method comprising administering to a mammal a composition, in an amount effective to inhibit tumor growth, the composition comprising a platinum complex having the formula

intercalated between the bilayers of a liposome, where the liposome comprises dioleyl phosphatidyl glycerol, and where DACH is diaminocyclohexane.

15. A liposomal antitumor composition comprising a platinum complex, the composition formed by a method, the method comprising adjusting the pH of a composition containing a liposome-entrapped first compound, so that the pH is made acidic, said first compound having the formula

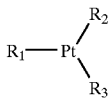

where $R_1$ is diaminocycloalkyl and $R_2$ and $R_3$ independently have the formula

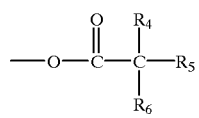

where $R_4$, $R_5$ and $R_6$ are each independently hydrocarbon moieties having from 1 to about 10 carbon atoms, and where said liposome comprises dioleyl phosphatidyl glycerol.

16. The liposomal antitumor composition of claim 15, wherein said adjusting comprises exposing the liposome-entrapped, first compound to a solution having an acidic pH.

17. The liposomal antitumor composition of claim 15 wherein the method further comprises before said adjusting step, the step of entrapping said first compound in said liposome.

18. The liposomal antitumor composition of claim 15 wherein said adjusting comprises reconstituting a lyophilized composition containing the liposome-entrapped first compound using an acidic solution.

19. The liposomal antitumor composition of claim 15 wherein said pH made acidic is between 2 and 6.5.

20. The liposomal antitumor composition of claim 15 wherein said adjusting comprises adding an acidic solution.

21. The liposomal antitumor composition of claim 20 wherein said acidic solution comprises sodium chloride.

22. The liposomal antitumor composition of claim 21 wherein said acidic solution is an aqueous solution.

23. A liposomal antitumor composition comprising a platinum complex, the composition formed by a method, the method comprising adjusting the pH of a composition containing a liposome-entrapped first compound, so that the pH is made acidic, said first compound having the formula

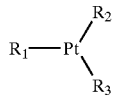

where $R_1$ is diaminocycloalkyl and $R_2$ and $R_3$ independently have the formula

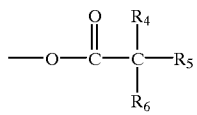

where $R_4$, $R_5$ and $R_6$ are each independently hydrocarbon moieties having from 1 to about 10 carbon atoms, said platinum complex having the formula

where $R_1$ is as defined above and X is halogen, and where said liposome comprises dioleyl phosphatidyl glycerol.

24. A liposomal antitumor composition comprising a platinum complex, the composition formed by a method, the method comprising adjusting the pH of a composition containing a liposome-entrapped first compound in the presence of sodium chloride, so that the pH is made acidic, said first compound having the formula

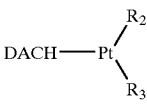

where DACH is 1,2-diaminocyclohexane and $R_2$ and $R_3$ independently have the formula

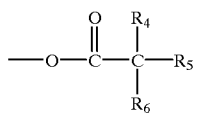

where $R_4$, $R_5$ and $R_6$ are each independently hydrocarbon moieties having from 1 to about 10 carbon atoms, said platinum complex having the formula

where DACH is as defined above, and where said liposome comprises dioleyl phosphatidyl glycerol.

25. The liposomal antitumor composition of claim 23 wherein said adjusting comprises adding an acidic solution.

26. The liposomal antitumor composition of claim 24 wherein said adjusting comprises adding an acidic solution.

27. A liposomal antitumor composition comprising a platinum complex, the composition formed by a method, the method comprising entrapping a first compound in a liposome comprising an acidic phospholipid that is dioleyl phosphatidyl glycerol to produce a liposomal composition, said first compound having the formula

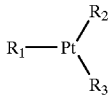

where $R_1$ is diaminocycloalkyl and $R_2$ and $R_3$ independently have the formula

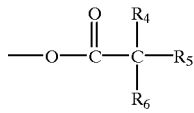

where $R_4$, $R_5$ and $R_6$ are each independently hydrocarbon moieties having from 1 to about 10 carbon atoms.

28. The liposomal antitumor composition of claim 27, wherein the method further comprises the steps of lyophilizing said liposomal composition to produce a lyophilized liposomal composition and reconstituting said lyophilized liposomal composition in an aqueous solution.

29. The liposomal antitumor composition of claim 27, wherein the method further comprises the steps of lyophilizing said liposomal composition to produce a lyophilized liposomal composition and reconstituting said lyophilized liposomal composition in a solution comprising sodium chloride.

30. The liposomal antitumor composition of claim 27, wherein the method further comprises the steps of lyophilizing said liposomal composition to produce a lyophilized liposomal composition and reconstituting said lyophilized liposomal composition in an acidic solution.

31. A liposomal antitumor composition comprising a platinum complex, the composition formed by a method, the method comprising entrapping a first compound in a liposome comprising an acidic phospholipid that is dioleyl phosphatidyl glycerol to produce a liposomal composition, said first compound having the formula

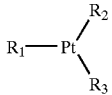

where $R_1$ is diaminocycloalkyl and $R_2$ and $R_3$ independently have the formula

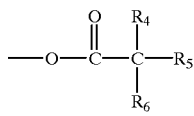

where $R_4$, $R_5$ and $R_6$ are each independently hydrocarbon moieties having from 1 to about 10 carbon atoms, said platinum complex having the formula

where $R_1$ is as defined above and X is halogen.

32. A liposomal antitumor composition comprising a platinum complex, the composition formed by a method, the method comprising entrapping a first compound in a liposome comprising an acidic phospholipid that is dioleyl phosphatidyl glycerol to produce a liposomal composition, said first compound having the formula

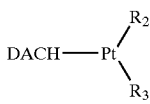

where DACH is 1,2-diaminocyclohexane and $R_2$ and $R_3$ independently have the formula

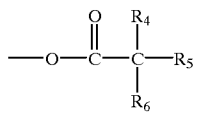

where $R_4$, $R_5$ and $R_6$ are each independently hydrocarbon moieties having from 1 to about 10 carbon atoms, said platinum complex having the formula

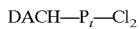

where DACH is as defined above.

33. The liposomal antitumor composition of claim 31 or 32 wherein the method further comprises the steps of lyophilizing said liposomal composition to produce a lyophilized liposomal composition and reconstituting said lyophilized liposomal composition in an aqueous solution.

34. The liposomal antitumor composition of claim 31 or 32 wherein the method further comprises the steps of lyophilizing said liposomal composition to produce a lyophilized liposomal composition and reconstituting said lyophilized liposomal composition in an acidic solution.

35. The method of claim 8, wherein said tumor is ovarian cancer, testicular cancer, lung cancer, cancer of the head or neck, esophageal cancer, bladder cancer, a sarcoma, a lymphoma or a mesothelioma.

36. The method of claim 14, wherein said tumor is ovarian cancer, testicular cancer, lung cancer, cancer of the head or neck, esophageal cancer, bladder cancer, a sarcoma, a lymphoma or a mesothelioma.

37. A method for treating cancer, the method comprising administering to a mammal in need thereof the composition of any one of claims 7, 15, 23, 24, 27, 31, or 32.

38. The method of claim 37, wherein said mammal is a human.

39. The method of claim 37, wherein said mammal has a cancer that is ovarian cancer, testicular cancer, lung cancer, cancer of the head or neck, esophageal cancer, bladder cancer, a sarcoma, a lymphoma or a mesothelioma.

40. A pharmaceutical composition comprising an amount of the composition of claim 1 effective to treat cancer and a pharmaceutically acceptable carrier or diluent.

41. A pharmaceutical composition comprising an amount of the composition of claim 7 effective to treat cancer and a pharmaceutically acceptable carrier or diluent.

42. A pharmaceutical composition comprising an amount of the composition of any one of claims 15, 23, 24, 27, 31 or 32 effective to treat cancer and a pharmaceutically acceptable carrier or diluent.

43. The liposomal antitumor composition of claim 15 wherein said adjusting is in the presence of sodium chloride.

44. A method for treating cancer, the method comprising administering to a mammal in need thereof the composition of any one of claims 16—22, 25, 26, 28, 20, 32.

* * * * *